United States Patent
Lin et al.

(10) Patent No.: US 8,512,532 B2
(45) Date of Patent: Aug. 20, 2013

(54) METHOD OF PRODUCING WHOLE BLOOD DETECTING ELECTRODE STRIP AND REACTION FILM FORMULATION AND THE RELATED PRODUCTS

(75) Inventors: Yueh-Hui Lin, Hsinchu (TW); Thomas Y. S. Shen, Hsinchu (TW)

(73) Assignee: Apex Biotechnology Corporation, Hsinchu (TW)

( * ) Notice: Subject to any disclaimer, the term of this patent is extended or adjusted under 35 U.S.C. 154(b) by 914 days.

(21) Appl. No.: 12/035,231

(22) Filed: Feb. 21, 2008

(65) Prior Publication Data
US 2008/0142362 A1    Jun. 19, 2008

Related U.S. Application Data

(62) Division of application No. 10/401,035, filed on Mar. 28, 2003, now Pat. No. 7,384,659.

(30) Foreign Application Priority Data

Mar. 29, 2002 (TW) ............................... 91106310 A
Mar. 24, 2003 (TW) ............................... 92106502 A

(51) Int. Cl.
*G01N 27/327* (2006.01)
(52) U.S. Cl.
USPC ....... 204/403.01; 204/400; 205/792; 205/787
(58) Field of Classification Search
USPC ............... 204/403.01, 403.02, 400; 205/792, 205/787
See application file for complete search history.

(56) References Cited

U.S. PATENT DOCUMENTS

| 4,876,205 A | 10/1989 | Green et al. |
| 5,385,846 A | 1/1995 | Kuhn et al. |
| 5,437,999 A | 8/1995 | Diebold et al. |
| 6,258,230 B1 | 7/2001 | Shen et al. |
| 2002/0048532 A1 | 4/2002 | Lin et al. |

FOREIGN PATENT DOCUMENTS

| CN | 1367382 | 9/2002 |
| EP | 1225449 | 7/2002 |

OTHER PUBLICATIONS

Methyl cellulose product information by Sigma-Aldrich (M0262, Jun. 3, 1997—CKV).*
Front matter and chapter 23 of the Paper Conservation Catalog by the American Institute for Conservation of Historic and Artistic Works—Book and Paper Group, sixth edition, Oct. 1989.*
Stephen Tillet "Technical Aids for systematic Botany III. More Ideas on Methyl-Cellulose Adhesives," Taxon 38(4): 597-601 Nov. 1989.*
Kuo et al., J. of Clinical Laboratory Analysis, 16:109-114, 2002.

* cited by examiner

*Primary Examiner* — Alex Noguerola
(74) *Attorney, Agent, or Firm* — Rothwell, Figg, Ernst & Manbeck, P.C.

(57) ABSTRACT

The present invention relates to a reaction film formulation used in the preparation of a non-enzymatic whole blood uric acid detecting electrode strip, which comprises an electron mediator, a water-soluble polymer carrier, and a volatile organic solvent, and to whole blood biosensor systems.

7 Claims, 3 Drawing Sheets

METHOD OF PRODUCING WHOLE BLOOD DETECTING ELECTRODE STRIP AND REACTION FILM FORMULATION AND THE RELATED PRODUCTS

CROSS REFERENCE TO RELATED APPLICATION

This application is a divisional of U.S. application Ser. No. 10/401,035 filed Mar. 28, 2003, which claims priority from R.O.C. application nos. 091106310 (filed Mar. 29, 2002) and 092106502 (filed Mar. 24, 2003). The disclosures of the above-referenced related applications are incorporated by reference herein in their entireties.

BACKGROUND OF THE INVENTION

1. Field of the Invention

The present invention relates to a method of producing a non-enzymatic whole blood detecting electrode strip, and the reaction film formulation comprising specific components that can be used in the production of said electrode strip.

2. Description of the Related Arts

Electrodes made by utilizing electrochemical methods can be divided into two types: enzymatic electrodes and non-enzymatic electrodes. At the present time, the majority of the electrodes mentioned in the technical literatures and used in the biological substances measuring are enzymatic electrodes, such as the well commercialized blood sugar electrode. In regard to non-enzymatic electrodes, most of them are used in the testing of general chemical compounds, such as pH electrodes for testing hydrogen ion. Since many enzymatic electrodes have restrictive conditions for moisture preservation, complicated manufacturing processes, and over-elaborate control conditions, manufacturing costs are quite high and mass production is not feasible, and thus they are only suitable for use by technicians in research organizations and large scale medical testing units.

Relating to the prior art of non-enzymatic electrode strips, such as an electric current non-enzymatic electrode strip disclosed in U.S. Pat. No. 6,258,230 B1, the manufacturing process uses screen printing to spread the reaction film formulation to cover two electrode systems. The composition of the reaction film formulation for being utilized in the screen printing requires large amounts of polymers mixed with a salt buffer. Although this type of electrodes can be used for mass production, there are numerous production steps, and the reaction film formulation is composed of many types of compositions, which lead to high production costs. Moreover, hemolytic phenomenon induced by the surfactant used in the reaction film formulation causes serious interference for the detection of uric acid in whole blood.

As a result, the market still has a need for the development of a method to producing a non-enzymatic whole blood detecting electrode strip.

SUMMARY OF THE INVENTION

One object of the present invention is to provide a method of producing a non-enzymatic whole blood detecting electrode strip.

Another object of the present invention is to provide a reaction film formulation used in the production of a non-enzymatic whole blood detecting electrode strip.

A further object of the present invention is to provide a non-enzymatic whole blood detecting electrode strip.

Another further object of the present invention is to provide a whole blood biosensor system.

DETAILED DESCRIPTION OF THE INVENTION

Figure 1A:
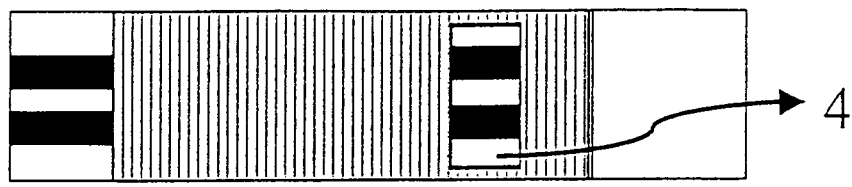
FIG. 1a shows a top view of the electrode strip in one embodiment of this present invention.

According to aforementioned deficiencies in the prior art, the applicants discovered that if the composition of the reaction film formulation is changed, and a dropwise addition method is used to replace the screen printing during production of the detecting electrode strip, the production steps can be simplified. The present invention utilizes a water solution that aids even dispersion to regulate the composition of the reaction film formulation, where only a very small amount of water-soluble polymer carrier is required and the use of a biologically active layer and salt buffer is not required, and the method can be changed to add dropwise the reaction film formulation onto the strip to produce a non-enzymatic whole blood detecting electrode strip.

In the prior art relating to the reaction layer of the whole blood detecting electrode strip, the teaching of the art only acknowledges the use of large amounts of surfactant to disrupt surface tension and evenly disperse the reaction layer. The present invention surprisingly found that the addition of a water solution into the reaction film formulation can result in the better dispersion of the reaction layer on the electrochemical reaction zone of the electrode strip. In addition, the mixture of the reaction film formulation of the inventive electrode strip is simplified, so as to shorten the production process of the reaction layer and increase the detecting precision of the electrode strip. According to the present invention, the electrode strip produced by the reaction film formulation can use a low operating potential of below 400 mV (0.4 V) to undergo electrochemical reactions to directly analyze the concentration of uric acid, hemoglobin or other components in a liquid sample.

Therefore, the first aspect of the present invention relates to the method of production of a non-enzymatic whole blood detecting electrode strip, including:

a. coating a conducting film on one side of an electrically insulating substrate to form an electrode system with an isolated and disconnected anode and cathode;

b. coating an electrically insulating film on a part of the anode and cathode of the electrode system, wherein one end of the anode uncovered with the conducting film forms at least a reference electrode and the other end forms an anode connector, one end of the cathode uncovered with the conducting film forms at least a working electrode and the other end forms a cathode connector, and an exposed part of the electrode system not covered with the insulating film forms an electrochemical reaction zone for forming a reaction layer; and c. adding dropwise a reaction film formulation onto the electrochemical reaction zone in step (b), and drying it to form the reaction layer, wherein the formulation comprise an electron mediator, a water-soluble polymer carrier, and a water solution used as a dispersing agent.

The "electron mediator" disclosed in the present invention refers to a substance that after reacting with the target to be tested in the whole blood sample (such as uric acid or hemoglobin), can itself be reduced from the oxidized state to the reduced state. When the electron mediator is changed into the reduced state, an external potential can be applied to the electrode strip to prompt the electron mediator return to the oxidized state from the reduced state. At this time, the variations of potential, resistance or current due to the chemical reaction can be transmitted to connections at the other ends of the electrode system by the working electrode and the reference electrode by contact with the conductive film and the reaction layer. When the whole blood detecting electrode strip is connected to a biosensing device, the biosensing device can apply an external potential to the electrode strip through a potential output device, receive the aforementioned change of potential, resistance or current due to the chemical reaction through a signal receiver, and convert the signal into the concentration of the target compound through a display device. According to a preferred embodiment of the present invention, the electron mediator can be potassium ferricyanide. More preferably, the amount of said electron mediator is from 0.05% to 6% of the reaction film formulation (calculated by weight). Even more preferably, when using said whole blood detecting electrode strip for the detection of uric acid, the amount of said electron mediator is about 0.3% of the reaction film formulation (calculated by weight), and when using said whole blood detecting electrode strip for the detection of hemoglobin, the amount of said electron mediator is about 3% of the reaction film formulation (calculated by weight).

The so-called "water-soluble polymer carrier" in the present invention refers to a substance that makes the electron mediator, once dried, adhere to the electric insulating substrate and strengthens the contact between the reaction layer and the liquid sample. More preferably, the molecular diameter of the water-soluble polymer carrier is smaller than 100 microns, thereby enabling the water-soluble polymer carrier to be dispersed evenly in the reaction film formulation solution and not easily to precipitate. After the reaction layer has been dried, if the distribution of the water-soluble polymer carrier is uneven, it will cause poor conductivity or functioning unevenly between the water-soluble electron mediator and the liquid sample, resulting in an inaccurate test result. More preferably, the water-soluble polymer carrier can be selected from the group consisting of polyvinyl acetate (PVA), polyvinyl pyrrolidone (PVP), polyethylene glycol (PEG), gelatin, carboxymethyl cellulose (CMC), methyl cellulose, and the mixture thereof. More preferably, the amount of the water-soluble polymer carrier is below 5% of the reaction film formulation (calculated by weight).

The so-called "dispersing agent" in the present invention refers to any dispersing agent that can aid the even dispersion of the abovementioned electron mediator and the water-soluble polymer carrier, such as a volatile organic solvent or a surfactant. Since the volatile organic solvent or the surfactant can disrupt the molecular cohesion of water, during the dropwise adding the reaction layer formation to the reaction zone of the electrode strip, it enables even distribution and avoids globule agglomeration. The appropriate dispersing agent can be chosen according to the target compound to be tested during the production of the present invention's reaction film formulation for the whole blood detecting electrode strip. According to the embodiment of the present invention, in the production of strips for the detection of uric acid, a volatile organic solvent agent can be chosen for the dispersing agent, and in the production of strips for the detection of hemoglobin, a surfactant is chosen for the dispersing agent.

According to an embodiment of the present invention, when the whole blood detecting electrode strip is used for detecting uric acid, the water solution to aid even dispersion is a solution that contains a volatile organic solvent. More preferably, the volatile organic solvent is selected from the group consisting of methyl alcohol, ethyl alcohol, ethyl ether, acetone and mixtures thereof. The amount of the volatile organic solvent is from 10% to 80% of the reaction film formulation (calculated by weight), even more preferably from 40% to 80%, and most preferably about 60%.

According to the embodiment of the present invention, when the whole blood detecting electrode strip is used for detecting hemoglobin, the water solution to aid even dispersion is a solution that contains a surfactant. More preferably, the surfactant is Triton X-100. The amount of the surfactant is from 1% to 6% of the reaction film formulation (calculated by weight), most preferably about 4%.

The so-called "insulating substrate" in the present invention refers to a thin-layered plate with a flat surface and electric insulating properties. More preferably, the insulating substrate is selected from the group consisting of polyvinyl chloride (PVC) plate, fiber glass (FR-4) plate, polyester sulphone, bakelite plate, polyester (PET) plate, polycarbonate (PC) plate, glass plate and ceramic plate (CEM-1).

The so-called "electrode system" in the present invention includes at least two metal electrodes that are isolated and disconnected from each other and used to connect the electric current biosensing device. According to the preferred embodiment of the present invention, the electrode system is partly covered by an electric insulating film, and one end of each of the two metal electrodes uncovered with the electric insulating film forms a working electrode and a reference electrode, and the other end of which forms connections of the working electrode and the reference electrode. The connections are used to connect the electric effect evoked during the electrochemical reaction caused by the testing sample and the aforementioned biosensing device. More preferably, the components used in the electrode system can include carbon paste, gold paste, silver paste, mixed carbon-silver paste, evaporated graphite or copper paste, or a combination thereof (e.g. screen printing of silver paste initially, followed by printing of carbon paste), or any conductive paste material that is suitable for screen printing and can be dried at below 80° C.

The so-called "insulating film" in the present invention refers to a thin layer formed by a material with electric insulating properties. According to a preferable embodiment of the present invention, the electric insulating film does not cover the reaction zone and the connections of the electrode system, and is formed on the substrate. More preferably, the insulating film has a thickness of 0.01 to 0.6 mm, and results in exposing the working electrode and the reference electrode on the insulating substrate not covered by the insulating film and forming an electrochemical reaction zone. The reaction zone is covered with a reaction layer 4 so as to become a dropwise position zone of the micro sample.

The so-called "reaction layer" in the present invention refers to the thin layer with an electrochemical reaction zone formed on the exposed part of the electrode system of the strip uncovered by the electric insulating film, that enables a reaction between the target in whole blood and the reaction film formulation added dropwise onto the electrochemical reaction zone.

In accordance with the production methods of the present invention, step (d) can be further included wherein a protection net is placed over the region of the reaction layer on the surface of the electric insulating film.

Figure 2A:
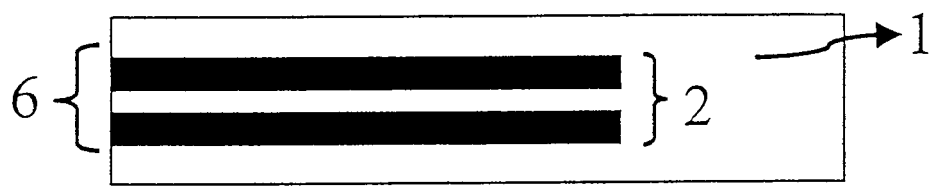
FIG. 2a shows the production steps of the electrode strip in one embodiment of this present invention, wherein there is an electrode system of at least two conduction rails on the insulating substrate.
Figure 2B:
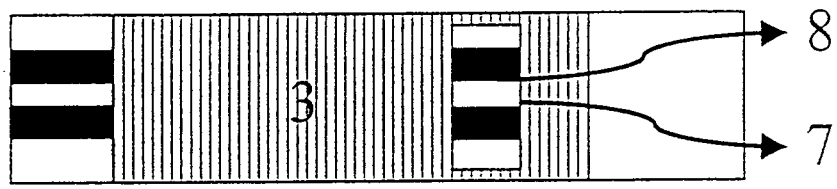
FIG. 2b shows the production steps of the electrode strip in one embodiment of this present invention, wherein the conductive film is partly covered by an electrically insulating film, leaving part of the conductive film exposed to form at least a two-conductive-rail electrode system, which contains the working electrode and reference electrode and the corresponding electric connection.
Figure 2C:
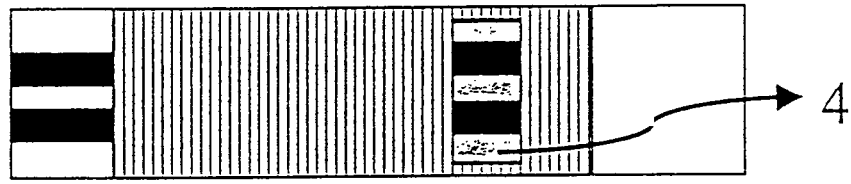
FIG. 2c shows the production steps of an exemplary electrode strip, wherein the reaction film formulation is placed on the exposed part of the insulating substrate not covered by the electrically insulating layer, and is then dried.

According to an exemplary method of production of the electrode strip of the present invention, as shown in FIG. 2a, firstly on any flat surface of the insulating substrate 1, at least two mutually isolated electrodes are positioned on the same surface of the insulating substrate to form an electrode system 2. In the second step of the production method of the present invention, as shown in FIG. 2b, an electric insulating film 3 of a thickness in the range of 0.01 to 0.6 mm is printed on the insulating substrate to cover parts of the electrode system, and parts of the electrode system not covered with the electric insulating layer form the connections 6, the working electrode 7, and the reference electrode 8. The region of the insulating substrate with the exposed working electrode 7 and the reference electrode 8 is the reaction layer region. In the third step, as shown in FIG. 2c, the reaction film formulation is added dropwise onto the electrochemical reaction zone to form the reaction layer 4.

Figure 2D:
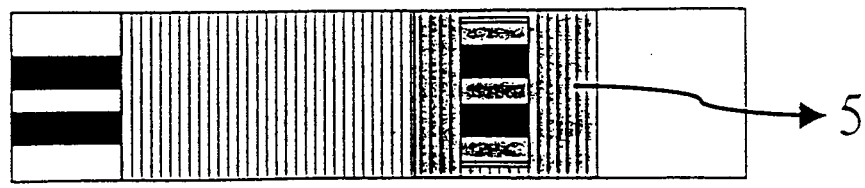
FIG. 2d shows the production steps of an exemplary electrode strip, wherein after drying of the reaction layer, a layer of protection net is placed over it.

In accordance with the methods of production of the electrode strip of the present invention, the aforementioned reaction layer can be further dried at below 80° C.; and according to situational requirements, as shown in FIG. 2d, a protection net 5 can be placed over the region of the reaction layer 4 on the surface of the aforementioned electric insulating film 3.

In addition, in regard to the reaction film formulation for the detection of uric acid, the applicants discovered that by altering the composition of the reaction film formulation so as to not contain a surfactant, interference with the detection of uric acid due to hemolytic in the sample being tested is avoided, and the use of biologically active substances (such as enzymes) is not required, and it decreases the amount of water-soluble polymer carriers, enables quicker drying at a lower temperature, increases production process efficiency and is consistent with the high sensitivity requirements of the production process so that the production costs are decreased.

Therefore, another aspect of the present invention is to provide a reaction film formulation used in the production of a non-enzymatic whole blood uric acid detecting electrode strip, which includes an electron mediator, water-soluble polymer carrier and a volatile organic solvent.

Another aspect of the present invention relates to a non-enzymatic whole blood detecting electrode strip produced by the aforementioned method.

Figure 1B:
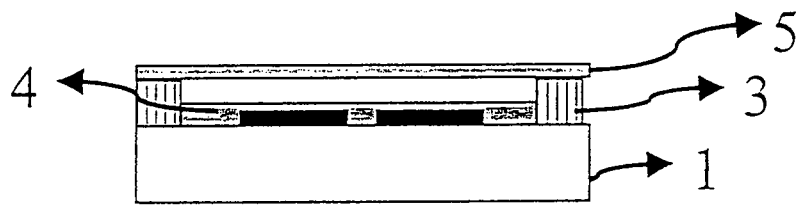
FIG. 1b shows a front view of the electrode strip in one embodiment of this present invention.

A diagram of a preferred embodiment of non-enzymatic whole blood detecting electrode strip of the present invention is shown in FIG. 1a and FIG. 1b. FIG. 1a and FIG. 1b are respectively the top view and the front view of the whole blood detecting electrode strip. The components approximately include the insulating substrate 1, the conductive film 2 located on the surface of the insulating substrate, the electric insulating film 3 partly covering the conductive film 2, and the reaction layer 4 that the electrochemical reaction occurs with the selected analyte. More preferably, a protection net 5 can be additionally placed over the electric insulating film of the whole blood detecting electrode strip in order to protect the reaction layer.

The fourth aspect of the present invention relates to a whole blood biosensor system that includes the aforementioned non-enzymatic whole blood detecting electrode strip and a biosensing device that can directly analyze the concentration of uric acid, hemoglobin or other substances in liquid or in whole blood. Based on the corresponding function of the reaction film formulation of the whole blood detecting electrode strip, for a uric acid detecting electrode strip, a suitable biosensing device can be collated with said strip to form the whole blood uric acid biosensor system, and for a hemoglobin strip, an appropriate biosensing device can be collocated with the strip to form the whole blood hemoglobin biosensor system.

The abovementioned biosensing device is comprised of a potential output unit, a signal receive and calculation unit, a display unit, and a strip connector. If the non-enzymatic whole blood detecting electrode strip described in the present invention is connected to the strip connector of the biosensing device, this enables the biosensor system to directly analyze the concentration of the target (such as uric acid or hemoglobin) in whole blood. After the electron mediator of the reaction layer has reacted with the target, and changed into the reduced state, the potential output device delivers a potential below 400 mV to the electrochemical reaction zone of the electrode strip inducing the release of electricity after the electron mediator is oxidized from the reduced state, then the electrode transmits the electric signal to the receive and calculation unit where the signal is converted, and returned to the display device, where the concentration of the target in whole blood is displayed.

The present invention is further described in detail by the following embodiments, which are only used to exemplify the present invention and are not to limit the scope of the present invention in any way. Any modifications and changes easily achieved by anyone skilled in the art are included in the scope of the subject patent application.

Embodiment 1: Production of Whole Blood Uric Acid Detecting Strip

A carbon paste electrode system 2 with a mutually isolated cathode and anode was screen printed onto the flat surface of a polyvinyl chloride (PVC) plate and then dried. Thereupon an insulating layer 3 of 0.5 cm in thickness was formed onto the same surface of the electrode system 2, leaving part of the conducting film exposed to form a connection 6, working electrode 7, and reference electrode 8. The exposed region not covered by the electric insulating film to form the working electrode 7 and reference electrode 8 is the electrochemical reaction zone.

Afterwards, the reaction film formulation prepared by mixing the water-soluble volatile organic solvent and the water-soluble polymer carrier and electron mediator mentioned below, was added dropwise using a dropper onto the aforementioned electrochemical reaction zone to form the reaction layer 4.

| Methyl cellulose (particle size: average of 20 microns) | 0.02% |
|---|---|
| Water | 39.95% |
| Potassium ferricyanide | 0.3% |
| Ethyl alcohol | 60% |

The reaction layer 4 was then dried. In addition, the reaction layer 4 on the surface of the electric insulating film 3 was covered by the protection net 5 to produce a whole blood uric acid detecting electrode strip that does not require biologically active components.

Figure 3:
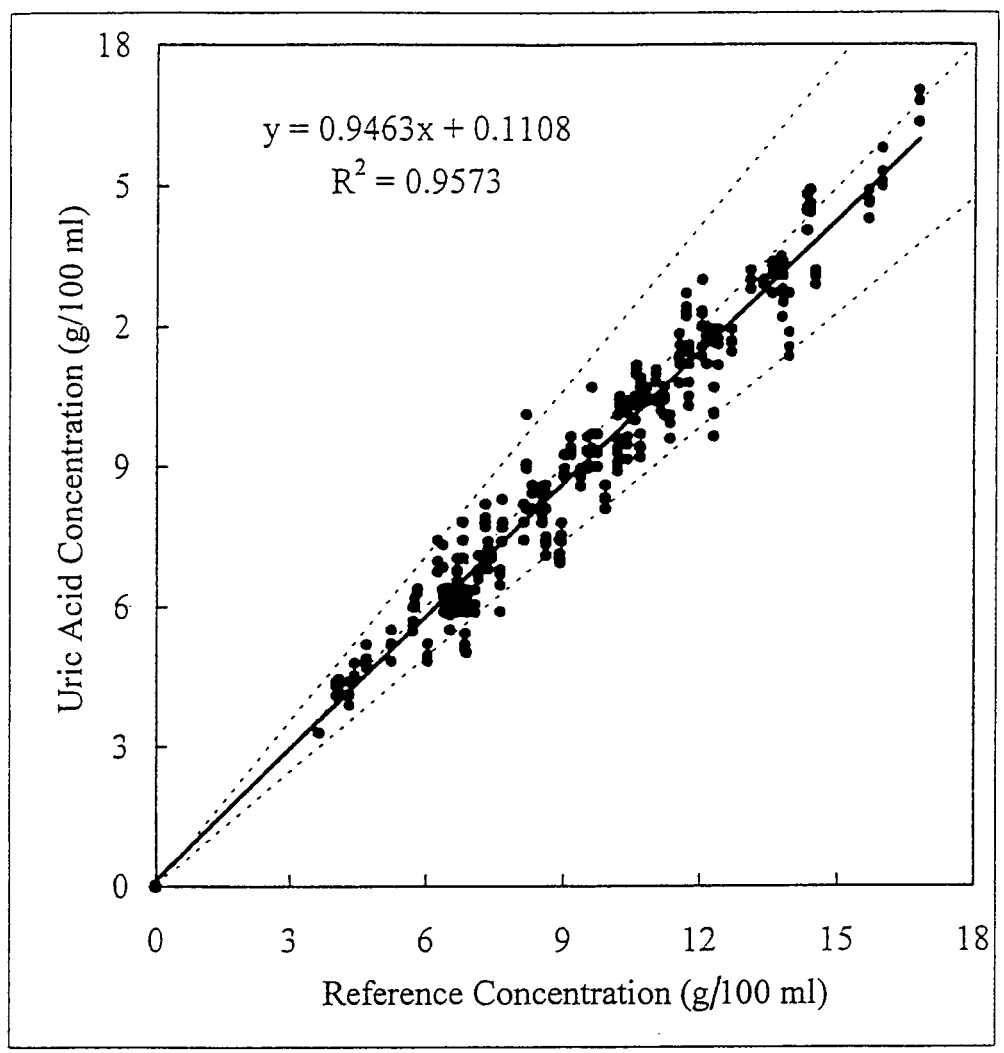
FIG. 3 shows a comparison of the concentrations of serum uric acid detected from the same samples by the present invention, and the eppendorf-EPAC 6140 biological analysis instruments and Roche-Uric Acid plus 1661868 reagent kit.

Embodiment 2: Efficiency of the Present Invention's Whole Blood Uric Acid Detecting Strip for Detecting Uric Acid Concentration The non-enzymatic uric acid detecting electrode strip produced was used to detect the concentration of uric acid in whole blood, the results of which are shown in FIG. 3. The test results of uric acid concentration from the present invention's uric acid detecting electrode strip were comparable to that of conventional methods (EPPENDORF-EPAC 6140 biological analysis instrument and ROCHE-Uric Acid plus 1661868 reagent kit). Therefore it is an evident that the present invention's non-enzymatic uric acid detecting electrode strip can accurately test the concentration of uric acid in blood and can be used to test whole blood directly without the need for preparatory steps.

Embodiment 3: Comparisons

The uric acid detecting strip produced from embodiment 1 and a uric acid detecting strip produced according to U.S. Pat. No. 6,258,230 were used to test and analyze the uric acid concentration in whole blood utilizing the same testing equipment, with the results shown in Table 1. In the six whole blood samples with different concentrations of uric acid, both strips were kept within ±10% of accuracy after comparison with the standard reference method; however, the precision of the present invention's uric acid detecting strip was clearly better than the detecting strip disclosed in the above-mentioned US patent, especially at low concentrations of uric acid (3-7 mg/100 ml, which is also within the normal range of conventional blood examination), with a coefficient of variation (% CV) maintained below 6.

Embodiment 4: Production of Whole Blood Detecting Hemoglobin Strip and the Efficiency of Such for Detecting Blood Hemoglobin Concentration Repeat the steps of embodiment 1 with replacement of the ingredients and proportion thereof with those below.

| Methyl cellulose (molecular size: average of 20 microns) | 0.02% |
|---|---|
| Water | 92.98% |
| Potassium ferricyanide | 3.0% |
| Triton X-100 | 4.0% |

Figure 4:
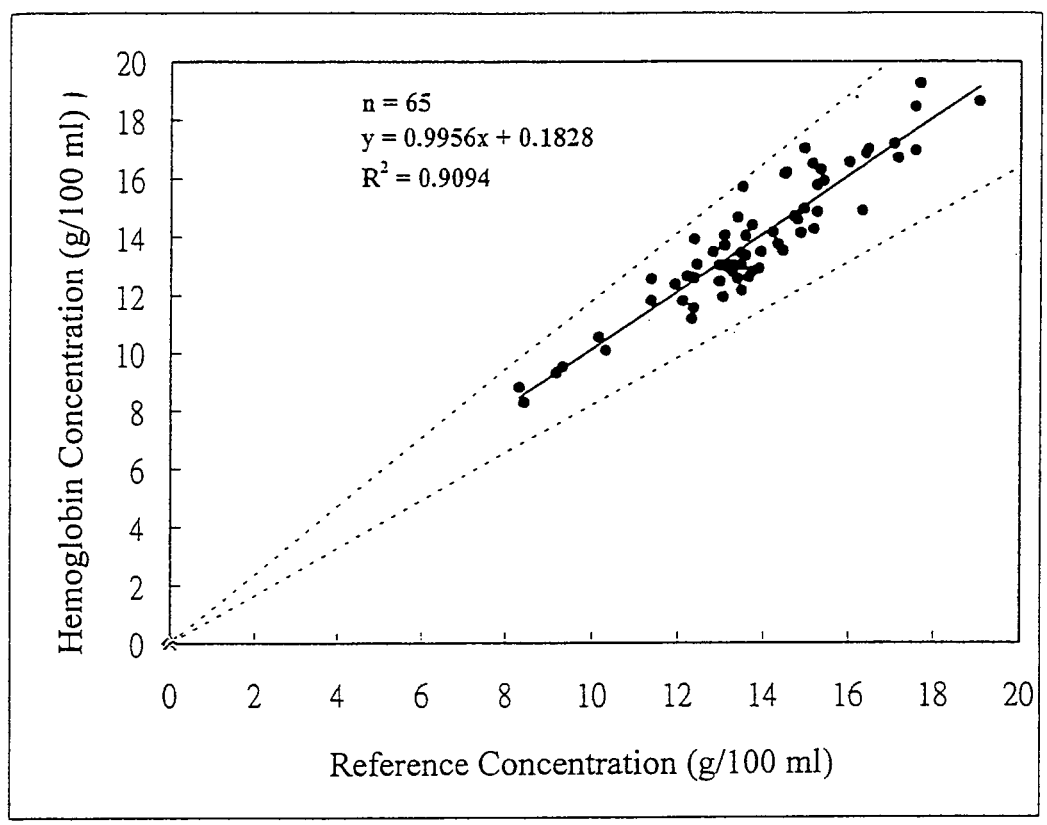
FIG. 4 shows a comparison of the results of the concentration of hemoglobin analyzed from the same samples by the present invention, and the SIGMA hemoglobin test and Metertek Spectrophotometer SP 8001.

Embodiment 5: Efficiency of Whole Blood Detecting Hemoglobin Strip on Detecting Concentration of Blood Hemoglobin The blood hemoglobin detecting electrode strip produced in embodiment 4 was used to test the concentration of hemoglobin in whole blood and the blood hemoglobin concentration obtained from the embodiment were compared to that obtained by the reference method of SIGMA hemoglobin test reagent kit and METERTEK spectrophotometer SP 8001 on the same blood sample, the results of which are shown in FIG. 4. Therefore, it is an evident that the present invention can accurately test the concentration of uric acid in whole blood.

Embodiment 6: Comparisons

The hemoglobin detecting strip produced from embodiment 4 and a hemoglobin detecting strip produced according to U.S. application Ser. No. 09/771,634 were used to test and analyze the hemoglobin concentration in whole blood utilizing the same testing equipment, with the results shown in Table 2. In the six whole blood samples with different concentrations of hemoglobin, both strips were kept within ±15% of accuracy after comparison with the standard reference method; however, the precision of the present invention's hemoglobin detecting strip was clearly better than the detecting strip disclosed in U.S. application Ser. No. 09/771,634, especially at low concentrations of hemoglobin (9-12 g/100 ml, which is also below the abnormal range in conventional blood examination), with a coefficient of variation (% CV) maintained below 6.

TABLE 1

|  |  | Whole blood sample | | | | | |
|---|---|---|---|---|---|---|---|
|  |  | 1 | 2 | 3 | 4 | 5 | 6 |
| Reference method (Uricase) (n = 2) | Average value (mg/100 ml) | 3.45 | 5.03 | 7.21 | 9.10 | 11.20 | 13.85 |
| Present invention's uric acid test strip (n = 10) | Average value (mg/100 ml) | 3.6 | 5.2 | 7.1 | 8.9 | 11.4 | 14.2 |
|  | % CV. | 4.8 | 4.5 | 3.5 | 3.2 | 4.6 | 2.1 |
| Uric acid test strip of U.S. Pat. No. 6,258,230 (n = 10) | Average value (mg/100 ml) | 3.5 | 5.6 | 6.8 | 8.9 | 11.5 | 14.0 |
|  | % CV. | 8.1 | 7.2 | 6.4 | 6.0 | 4.5 | 4.5 |

TABLE 2

| | | Whole blood sample | | | | | |
|---|---|---|---|---|---|---|---|
| | | 1 | 2 | 3 | 4 | 5 | 6 |
| Reference method (met-Hb) (n = 2) | Average value (g/100 ml) | 9.82 | 12.14 | 14.70 | 16.15 | 18.44 | 20.03 |
| Hemoglobin test strip of present invention (n = 10) | Average value (g/100 ml) | 10.6 | 12.39 | 14.8 | 15.8 | 18.6 | 19.7 |
| | % CV. | 5.8 | 5.6 | 4.5 | 4.8 | 4.6 | 3.1 |
| Hemoglobin test strip of ROC Patent No. 145439 (n = 10) | Average value (g/100 ml) | 10.5 | 12.6 | 14.5 | 16.2 | 11.5 | 19.6 |
| | % CV. | 9.3 | 7.2 | 5.6 | 4.5 | 4.2 | 3.5 |

From the abovementioned embodiments, it is a clearly evident that the present invention's whole blood detecting electrode strip, which does not require a biologically active layer, can simplify electrode production steps and can shorten the production process and increase efficiency, and moreover can control the electrode reaction at a low potential of below 400 mV and can be used directly on whole blood as a non-enzymatic method to accurately analyze the concentration of uric acid, hemoglobin or other substances in whole blood.

What is claimed is:

1. A non-enzymatic whole blood electrode strip, which is produced by a method comprising the steps of:
    (a) coating a conducting film on one side of an electrically insulating substrate to form an electrode system with an isolated and disconnected anode and cathode;
    (b) coating an electrically insulating film on a part of the anode and cathode of the electrode system, wherein one end of the anode uncovered with the conducting film forms at least a reference electrode and the other end forms an anode connector, and one end of the cathode uncovered with the conducting film forms at least a working electrode and the other end forms a cathode connector; and an exposed part of the electrode system not covered with the insulating film forms an electrochemical reaction zone for forming a reaction layer; and
    (c) adding dropwise a reaction film formulation onto the electrochemical reaction zone in step (b), and drying it to form the reaction layer; wherein the formulation comprise an electron mediator, a water-soluble polymer carrier and a volatile organic solvent used as a dispersing agent, and wherein the amount of the electron mediator is from 0.05% to 6% of the reaction film formulation calculated by weight, the amount of the water-soluble polymer carrier is below 5% of the reaction film formulation calculated by weight, and the amount of the volatile organic solvent is from 10% to 80% of the reaction film formulation calculated by weight, wherein the formulation does not contain a surfactant; and
    wherein the non-enzymatic whole blood electrode strip is used for detecting uric acid.

2. A whole blood biosensor system, which comprises the non-enzymatic whole blood detecting electrode strip according to claim 1 and a biosensing device.

3. The non-enzymatic whole blood electrode strip according to claim 1, wherein the electron mediator is potassium ferricyanide.

4. The non-enzymatic whole blood electrode strip according to claim 1, wherein the molecular diameter of the water-soluble polymer carrier is less than 100 microns.

5. The non-enzymatic whole blood electrode strip according to claim 1, wherein the water-soluble polymer carrier is selected from the group consisting of polyvinyl acetate, polyvinyl pyrrolidone, polyethylene glycol, gelatin, carboxymethyl cellulose, methyl cellulose and the mixture thereof.

6. The non-enzymatic whole blood electrode strip according to claim 1, wherein the volatile organic solvent is selected from the group consisting of methyl alcohol, ethyl alcohol, ethyl ether, acetone and the mixture thereof.

7. The non-enzymatic whole blood electrode strip according to claim 1, wherein the amount of the volatile organic solvent is about 60% of the reaction film formulation calculated by weight.

* * * * *